United States Patent [19]

Erpenbach et al.

[11] Patent Number: 4,664,753

[45] Date of Patent: May 12, 1987

[54] PROCESS FOR SEPARATING IODINE AND ITS COMPOUNDS FROM THE CARBONYLATION PRODUCTS OBTAINED BY SUBJECTING DIMETHYLETHER, METHYL ACETATE OR METHANOL TO A CARBONYLATION REACTION

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 637,860

[22] Filed: Aug. 6, 1984

[30] Foreign Application Priority Data

Aug. 18, 1983 [DE] Fed. Rep. of Germany ....... 3329781

[51] Int. Cl.$^4$ .................. C07C 51/44; C07C 51/573; C07C 67/54
[52] U.S. Cl. .......................... 203/29; 203/38; 260/546; 260/549; 560/232; 560/248; 562/608
[58] Field of Search ............... 562/608; 560/248, 232; 260/549, 546; 203/38, 29, 31-33

[56] References Cited

U.S. PATENT DOCUMENTS

| | | | |
|---|---|---|---|
| 3,084,109 | 4/1963 | Ure et al. | 562/608 |
| 3,709,795 | 1/1973 | Singleton | 203/31 |
| 3,772,156 | 11/1973 | Johnson et al. | 203/33 |
| 3,884,965 | 5/1975 | Kollar | 560/248 |
| 4,115,444 | 9/1978 | Rizkalla | 260/549 |
| 4,246,195 | 1/1981 | Szecsi | 560/232 |
| 4,333,884 | 6/1982 | Kubbeler et al. | 260/549 |
| 4,430,273 | 2/1984 | Erpenbach et al. | 260/549 |
| 4,497,747 | 2/1985 | Vogt et al. | 260/549 |

FOREIGN PATENT DOCUMENTS

| | | | |
|---|---|---|---|
| 0013551 | 11/1981 | European Pat. Off. | |
| 0059367 | 5/1984 | European Pat. Off. | |
| 1558942 | 3/1969 | France | 562/608 |
| 83315 | 7/1975 | Japan | 562/608 |
| 101310 | 9/1978 | Japan | 562/608 |
| 132516 | 10/1979 | Japan | 562/608 |

Primary Examiner—Wilbur Bascomb
Attorney, Agent, or Firm—Connolly & Hutz

[57] ABSTRACT

The disclosure relates to a process for separating iodine and its compounds from the carbonlyation products acetic acid, acetic anhydride or ethylidene diacetate obtained by subjecting dimethylether, methyl acetate or methanol to a carbonylation reaction. For reducing the quantity of total iodine contaminating the carbonylation products to less than 20 ppb iodine, the disclosure provides for the carbonylation products to be treated at temperatures of 20° to 250° C. with an alkyl or aryl phosphine or a heterocyclic aromatic nitrogen compound and at least one of the metals copper, silver, zinc or cadmium or their compounds and to be distillatively separated from the iodine thereby fixed in non-volatile form.

8 Claims, No Drawings

PROCESS FOR SEPARATING IODINE AND ITS COMPOUNDS FROM THE CARBONYLATION PRODUCTS OBTAINED BY SUBJECTING DIMETHYLETHER, METHYL ACETATE OR METHANOL TO A CARBONYLATION REACTION

The present invention relates to a process for separating iodine and its compounds from the carbonylation products acetic acid and/or acetic anhydride and/or ethylidene diacetate obtained by subjecting dimethylether and/or methyl acetate and/or methanol to a carbonylation reaction.

German Specification No. DE-B-21 04 828 describes a process for removing minor quantities of halide contaminants from acetic acid preferably made by reacting an alcohol or olefin with carbon monoxide in the presence of a catalyst system comprised of a noble metal component and a halogen component by subjecting the acid to treatment with potassium permanganate, sodium permanganate, potassium dichromate, sodium dichromate, chromium trioxide, chromium potassium oxalate, potassium chlorochromate, potassium chlorate and/or potassium chromate at 16° to 200° C. More particularly, acetic acid containing less than 500 ppb halide, especially iodide, is contacted, prior to or while distilling it, with one of the metal compounds aforesaid which is used in a proportion of up to 1.0 weight %, based on acetic acid, 90 to 98% of the halide compound becoming separated. Carbonylation products containing acetic anhydride cannot so effectively be purified by the process just described as the oxidants specified react also with acetic anhydride and then fail to fix the iodide.

German Specification No. DE-AS 22 56 510 discloses a process for removing very minor quantities of iodide from acetic acid wherein the acetic acid is freed from iodine-containing compounds in a system comprising two distilling columns by adding an oxide, hydroxide, carbonate, bicarbonate and a salt of a weak organic acid of an alkali metal or alkaline earth metal as well as a mixture of alkali metal or alkaline earth metal compounds, with hypophosphorous acid, the acid so treated presenting a residual iodine content of less than 40 ppb to less than 5 ppb, depending on the initial iodine content. In this process, the salts of the alkali metals and alkaline earth metals and also the hypophosphorous acid are used in the form of an aqueous solution. As results, the purification method just described is of little use for freeing acetic anhydride from iodine compounds contaminating it, as the anhydride undergoes saponification.

German Specification No. DE-A-29 01 359 describes a process for removing iodine from organic compounds, wherein the iodine-containing compounds are treated at 50° to 200° C. with an oxidant and the reaction mixture is contacted, during or after that treatment, with an adsorbant. The oxidants which are preferably used are oxygen or hydrogen peroxide and the adsorbant is active carbon. Hydrogen peroxide of 20% strength is the oxidant used in the working examples of that Specification. 92.4 to 99.5% of the iodine is removed, the residual iodine content being still as high as .40 ppm which definitely fails to comply with purity requirements. Once again, water is introduced into the system by the use of hydrogen peroxide, which is disadvantageous.

German Specification No. DE-A-31 07 731 describes a process for separating organic iodine compounds from carbonylation products of methanol, methyl acetate and dimethylether by liquid phase extraction with a non-aromatic hydrocarbon. As disclosed in the working examples of that specification, the iodine contents are reduced to at most 100 ppb iodine. Apart from the fact that these iodine values are too high, the process entails considerable expenditure resulting from the additional distilling step the extractant is subjected to.

German Specification No. DE-A-29 40 751 teaches removing iodine compounds from carbonylation products of methyl acetate by subjecting these latter to treatment with cesium, potassium and/or sodium acetates with the resultant formation of the corresponding alkali metal iodides. The methyl iodide-reduction to just 2 ppm does not satisfy the requirements a purified carbonylation product has to meet for workup. It is incidentally not possible by gas-chromatographic analysis, based on methyl iodide, accurately to determine the total iodine contained in the carbonylation product so that it is really difficult to make a definite statement relative to the iodine separation actually achieved.

The present invention now provides a process permitting alkyl and aryl iodides or other easily distillable iodine-containing compounds to be removed and also iodine in whatever chemically combined or elemental form to be fixed and to be almost quantitatively separated from the feed product to be purified. Exemplary representatives of removable iodine compounds are methyl iodide, butyl iodide, iodo acetone, iodo benzene, acetyl iodide, benzoyl iodide, hydrogen iodide and, optionally, substituted ammonium and phosphonium iodides.

The process of this invention comprises more especially: reducing the quantity of total iodine contaminating the carbonylation products to less than 20 ppb iodine by treating the carbonylation products at temperatures of 20° to 250° C. with an alkyl or aryl phosphine or a heterocyclic aromatic nitrogen compound and at least one of the metals copper, silver, zinc or cadmium or their compounds, and distillatively separating them from the iodine thereby fixed in non-volatile form.

Further preferred and optional features of the present process provide:

(a) for carbonylation products containing less than 500 ppm total iodine to be used;

(b) for the carbonylation products to be treated at temperatures of 100° to 140° C. over a period of 15 to 120 minutes;

(c) for a ratio by weight of iodine(-compound) to alkyl and/or aryl phosphine and/or nitrogen compound to metal(-compound) of 1:(100–10 000):(50–10 000) to be established in the mixture to be treated;

(d) for the carbonylation products to be treated in the presence of hydrogen.

The fixation of the iodine-containing contaminants should conveniently be effected by adding the necessary mixture e.g. of triphenyl-phosphine and copper(II)acetate ahead of the last purification stage in which high-boiling residue is removed from the carbonylation product desired to be made. The iodine-containing compounds are removed with distillative separation of the purified product via the base fraction, jointly with the high-boiling residue. Used mixture can be admixed e.g. with fresh triphenylphosphine and copper(II)acetate and recycled together with a portion of base product for re-use.

Needless to say, it is also possible for untreated product with less than 500 ppm, preferably less than 10 ppm of contaminating iodine-containing compounds therein, which is taken from the last purification stage in the entire carbonylation process, to be subjected to treatment e.g. with triphenyl-phosphine and copper(II)acetate so as to be freed from these contaminants.

The process of this invention permits the total iodine content in the treated carbonylation product to be reduced beyond the limit of detection of less than 5 ppb (=5 parts by weight iodine per a billion ($10^9$) parts by weight carbonylation product).

The useful alkyl and arylphosphines comprise more especially tributylphosphine, trioctylphosphine, trilaurylphosphine and triphenylphosphine; useful heterocyclic aromatic nitrogen compounds are pyridine, N-methylimidazol, 3-picoline, 2,4-lutidine, 3,4-lutidine and quinoline. Acetates should preferably be employed as metal compounds. It is also possible however to use oxides or acetylacetonates in combination with the alkyl and/or arylphosphines and/or aromatic nitrogen compounds for the fixation of undesirable iodine-containing compounds. If zinc is used, it should conveniently be employed as metallic material.

The ratio by weight of iodine(-compound) to alkyl and/or aryl phosphines and/or nitrogen compound to metal(-compound) can be varied within wide limits. It is good practice however for reasons of economy to use a ratio not excessively beyond 1:6000:6000.

The carbonylation product can be treated at atmospheric or increased pressure. The result is favorably influenced by the addition of minor quantities of hydrogen.

The process of this invention can be effected in continuous or discontinuous manner.

The total iodine is analytically determined by an iodine-catalyzed reaction between arsenic and cerium ions with photometric terminal determination of cerium.

EXAMPLE 1

100 g acetic anhydride contaminated with 1 ppm total iodine was admixed with 0.5 g triphenylphosphine and 0.3 g copper(II)acetate and stirred for 1.5 hours at 135° C. Next, the acetic anhydride was distilled off and analyzed. The total iodine content was beyond the limit of detection of less than 0.005 ppm (less than 5 ppb=less than 5 pp $10^9$), corresponding to the separation of more than 99.5% iodine.

EXAMPLE 2

(Comparative Example)

100 g acetic anhydride contaminated with 1 ppm total iodine was admixed with 0.5 g triphenylphosphine and stirred for 1.5 hours at 135° C. Next, the mixture was distilled. 0.15 ppm total iodine was determined in the acetic anhydride passing over as the distillate. 85% iodine, based on the iodine intially present was separated.

EXAMPLE 3

(Comparative Example)

100 g acetic anhydride contaminated with 1 ppm total iodine was admixed with 0.3 g copper(II)acetate and stirred for 1.5 hours at 135° C. Next, the acetic anhydride was distilled off and analyzed. 0.15 ppm total iodine content was determined, corresponding to an iodine separation of 85%, based on the iodine initially present.

EXAMPLE 4

100 g acetic acid contaminated with 3 ppm elemental iodine was heated for 1 hour under reflux with 1 g triphenylphosphine and 0.5 g copper(II)acetate. Next, the acetic acid was distillatively separated from the mixture and analyzed. It contained 9 ppb iodine, corresponding to the separation of 99.7% iodine.

EXAMPLE 5

100 g acetic anhydride contaminated with 2.0 ppm total iodine, 0.5 g triphenylphosphine and 0.2 g zinc powder were placed in a 250 ml round flask and heated for 1.0 hour to 135° C. Next, the acetic anhydride so treated with distillatively separated from the mixture and its total iodine content was determined by analysis. It was less than 5 ppb, corresponding to a separation of more than 99.8% iodine.

EXAMPLE 6

100 g acetic anhydride contaminated with 1.0 ppm total iodine, 0.5 g triphenylphosphine and 0.5 g cadmium(II)acetate were placed in a 250 ml round flask and stirred for 2 hours at 135° C. Next, the acetic anhydride so treated was distilled off and analyzed. It contained 10 ppb total iodine, corresponding to a separation of 99.0% iodine, based on the iodine initially present.

EXAMPLE 7

100 g acetic anhydride containing 40 ppm total iodine, 3.0 g triphenylphosphine and 3.0 g copper(II)acetate were weighed into a 250 ml round flask and stirred for 1.5 hours at 135° C. Next, the acetic anhydride so treated was distillatively separated from the iodine compounds fixed during that treatment and also from the mixture in excess. The separated acetic anhydride contained 7 ppb total iodine, corresponding to the separation of more than 99.9% iodine.

EXAMPLE 8

100 g acetic anhydride contaminated with 2.5 ppm total iodine, 1.0 g triphenylphosphine and 1 g copper acetylacetonate were weighed into a 250 ml round flask and stirred for 0.5 hour at 135° C. Next, the acetic anhydride so treated was distillatively separated from the iodine compounds fixed during that treatment, and analyzed. The total iodine content was beyond the limit of detection of less than 5 ppb, corresponding to a separation of more than 99.8% iodine.

EXAMPLE 9

100 g acetic anhydride contaminated with 70 ppm total iodine, 3 g triphenylphosphine and 1.5 g zinc powder were stirred for 1.5 hours at 135° C. Next, the acetic anhydride was distillatively separated and analyzed. It contained 15 ppb total iodine, corresponding to a separation of more than 99.9% iodine.

EXAMPLE 10

100 g acetic anhydride contaminated with 3 ppm total iodine, 0.7 g triphenylphosphine and 0.5 g silver acetate were stirred for 0.75 hour at 135° C. Next, the acetic anhydride was distillatively separated and a distillate containing 7 ppb total iodine corresponding to the separation of 99.8% iodine, was obtained.

EXAMPLE 11

100 g acetic anhydride contaminated with 2 ppm total iodine, 0.5 g triphenylphosphine and 0.2 g copper(II-)acetate were weighed into a 250 ml round flask and heated for 2 hours to 110° C. Next, the acetic anhydride so treated was distillatively separated from the mixture and its total iodine content was determined by analysis. It was 5 ppb, corresponding to the separation of 99.8% iodine.

EXAMPLE 12

100 g acetic anhydride contaminated with 2.5 ppm total iodine was mixed with 0.3 g N-methylimidazol and 0.5 g copper(II)acetate and the mixture was stirred for 2.0 hours at 135° C. Next, the anhydride was distilled off and analyzed. It contained 15 ppb total iodine, corresponding to the separation of 99.4% iodine.

EXAMPLE 13

100 g acetic anhydride contaminated with 2.5 ppm total iodine, 0.75 g 2,4-lutidine and 0.5 g zinc powder were weighed into a 250 ml round flask and stirred for 1.5 hours at 135° C. Next, the acetic anhydride was distilled off and analyzed. It contained 10 ppb total iodine, corresponding to the separation of 99.6% iodine.

EXAMPLE 14

100 g acetic anhydride contaminated with 1 ppm total iodine was admixed with 0.3 g tributylphosphine and 0.3 g copper(II)acetate and the mixture was stirred for 2.0 hours at 125° C. Next, the acetic anhydride was distilled off and analyzed. It contained 10 ppb total iodine, corresponding to the separation of 99.0% iodine.

EXAMPLE 15

100 g acetic anhydride contaminated with 2 ppm total iodine was admixed with 0.3 g tributylphosphine and 0.3 g copper(II)-acetate and the mixture was stirred for 2 hours at 125° C. During that period, 2 liters/h (S.T.P) hydrogen was passed through the mixture. Next, the acetic anhydride was distilled off and analyzed. It contained less than 5 ppb total iodine, corresponding to the separation of more than 99.8% iodine.

We claim:

1. A process for separating iodine and its compounds from the carbonylation products acetic acid, acetic anhydride or ethylidene diacetate obtained by subjecting dimethylether, methyl acetate or methanol to a carbonylation reaction, which process comprises: reducing the quantity of total iodine contaminating the carbonylation products to less than 20 ppb iodine by treating the carbonylation products at temperatures of 20° to 250° C. with an alkyl or aryl phosphine or a heterocyclic aromatic nitrogen compound and at least one of the metals copper, silver, zinc or cadmium or their compounds and distillatively separating the carbonylation products from the iodine thereby fixed in nonvolatile form.

2. A process as claimed in claim 1, wherein carbonylation products containing less than 500 ppm total iodine are used.

3. A process as claimed in claim 1, wherein the said treating of the carbonylation products is carried out at temperatures of 100° to 140° C. over a period of 15 to 120 minutes.

4. A process as claimed in claim 1, wherein a ratio by weight of iodine(-compound) to alkyl- or aryl phosphine or nitrogen compound to metal(-compound) of 1:(100–10 000):(50–10 000) is established in the mixture to be treated.

5. A process as claimed in claim 1, wherein said treating of the carbonylation products is carried out in the presence of hydrogen.

6. A process as claimed in claim 1, wherein the aryl phosphine is triphenylphosphine, and the heterocyclic aromatic nitrogen compound is pyridine, N-methylimidazole, 3-picoline, 2,4-lutidine, 3,4-lutidine, or quinoline.

7. A process as claimed in claim 1, wherein the metal or metal compound is (a) metallic zinc or (b) an acetate, an oxide, or an acetyl acetonate of copper, cadmium or silver.

8. A process as claimed in claim 7, wherein the phosphine is triphenyl-phosphine and the metal compound is copper(II)acetate.

* * * * *